United States Patent [19]

Bohmfalk

[11] Patent Number: 5,694,927
[45] Date of Patent: Dec. 9, 1997

[54] DISPOSABLE MASK AND SUCTION CATHETER

[76] Inventor: George L. Bohmfalk, #3 Pine Creek Pl., Texarkana, Tex. 75503

[21] Appl. No.: 555,148

[22] Filed: Nov. 8, 1995

[51] Int. Cl.$^6$ .................. A61M 16/00; A62B 18/00
[52] U.S. Cl. .................. 128/206.19; 128/205.27; 128/206.21; 128/206.22; 128/863
[58] Field of Search .................. 128/863, 206.19, 128/201.23, 201.29, 205.27, 206.15, 206.21, 910, 206.22

[56] References Cited

U.S. PATENT DOCUMENTS

| | | | |
|---|---|---|---|
| D. 327,141 | 6/1992 | Hubbard et al. | D29/9 |
| D. 347,713 | 6/1994 | Brunson | D29/8 |
| 735,959 | 8/1903 | Folkmar | 128/200.28 |
| 1,292,096 | 1/1919 | Schwartz . | |
| 1,463,390 | 7/1923 | Fernandes | 128/863 |
| 1,491,674 | 4/1924 | Coletti . | |
| 2,376,871 | 5/1945 | Fink | 128/146 |
| 2,617,415 | 11/1952 | Rosen et al. | 128/205 |
| 2,848,994 | 8/1958 | Aguado | 128/146 |
| 2,859,748 | 11/1958 | Hudson | 128/146 |
| 2,921,581 | 1/1960 | Swearingen | 128/206.27 |
| 2,954,027 | 9/1960 | Marasco | 128/195 |
| 3,130,722 | 4/1964 | Dempsey et al. | 128/143 |
| 3,247,599 | 4/1966 | O'Connor | 33/185 |
| 3,249,108 | 5/1966 | Terman | 128/146 |
| 3,288,138 | 11/1966 | Sachs | 128/139 |
| 3,315,672 | 4/1967 | Cunningham | 128/139 |
| 3,529,594 | 9/1970 | Charnley | 128/863 |
| 3,625,207 | 12/1971 | Agnew | 128/863 |
| 3,747,599 | 7/1973 | Malmin | 128/139 |
| 3,804,086 | 4/1974 | Agnew | 128/146.2 |
| 3,827,433 | 8/1974 | Shannon | 128/145.5 |
| 3,877,691 | 4/1975 | Foster | 269/322 |
| 3,890,966 | 6/1975 | Aspelin et al. | 128/146.2 |
| 3,955,570 | 5/1976 | Hutter, III | 128/201.23 |

(List continued on next page.)

FOREIGN PATENT DOCUMENTS

| | | | |
|---|---|---|---|
| 0018805 | 11/1980 | European Pat. Off. | A61B 19/00 |
| 0081943 | 6/1983 | European Pat. Off. | A61B 19/00 |
| 0390856 | 6/1989 | European Pat. Off. | A61F 9/00 |
| 56-18096 | 4/1981 | Japan | A61B 19/00 |
| 57-1932 | 1/1982 | Japan | A61B 19/00 |
| 57-4 | 1/1982 | Japan | A61B 19/00 |
| 57-5 | 1/1982 | Japan | A61B 19/00 |
| 62-97904 | 5/1987 | Japan | A61B 19/00 |
| 2264060 | 8/1993 | United Kingdom | A62B 18/02 |
| 9402190 | 2/1994 | WIPO | 128/201.23 |
| 9618918 | 6/1996 | WIPO | G02B 1/10 |

OTHER PUBLICATIONS

Preul, et. al., "Neurosurgeon as innovator: William V. Cone (1897–1959)"; *Journal of Neurosurgery*, vol. 79, 619:631, Oct. 1993; p. 626.
VHA, Inc., "VHAPlus Face Masks" advertising brochure, Model V1025.
VHA Plus Face Mask, Model V1025.
Tecnol, Inc. "The Mask Collection" advertising brochure.
Tecnol, Inc., "PCM2000 Submicron Face Mask" advertising brochure.
Tecnol, inc. PCM2000 Submicron Face Mask.
Tecnol, Inc. "Operation and Service Manual," Aug. 1993 PortaCount Plus Model 8020.

*Primary Examiner*—Vincent Millin
*Assistant Examiner*—V. Srivastava
*Attorney, Agent, or Firm*—Robert Hardy Falk; Tom R. Vestal; Falk & Fish, l.l.p.

[57] ABSTRACT

A disposable mask and suction catheter includes a mask having a front side and a back side, the back side being disposed in contact with a user's face during use. The disposable mask and suction catheter also includes a catheter tube having a first and a second end, the first end being removably attachable to a suction source for removing exhaled air and the second end being attached to the back side of the mask. The disposable mask and suction catheter helps to prevent fogging of glasses or other eyewear due to moist, exhaled air that escapes from behind the mask, and improves user comfort by constantly removing the warm, moist air behind and around the mask and drawing cool, dry air into the mask.

27 Claims, 1 Drawing Sheet

U.S. PATENT DOCUMENTS

| | | | |
|---|---|---|---|
| 3,974,829 | 8/1976 | Tate, Jr. | 128/146.2 |
| 4,019,508 | 4/1977 | Der Estephanian et al. | 128/142.7 |
| 4,037,593 | 7/1977 | Tate, Jr. | 128/146.2 |
| 4,055,173 | 10/1977 | Knab | 128/201.29 |
| 4,082,092 | 4/1978 | Foster | 128/139 |
| 4,150,443 | 4/1979 | McNeilly | 2/436 |
| 4,296,746 | 10/1981 | Mason, Jr. et al. | 128/201.15 |
| 4,361,146 | 11/1982 | Woicke | 128/206.12 |
| 4,419,993 | 12/1983 | Petersen | 128/201.15 |
| 4,469,097 | 9/1984 | Kelman | 128/205.24 |
| 4,583,535 | 4/1986 | Saffo | 128/201.25 |
| 4,589,408 | 5/1986 | Singer | 128/132 R |
| 4,606,341 | 8/1986 | Hubbard et al. | 128/206.19 |
| 4,635,628 | 1/1987 | Hubbard et al. | 128/201.17 |
| 4,641,645 | 2/1987 | Tayebi | 128/206.19 |
| 4,643,182 | 2/1987 | Klein | 128/201.25 |
| 4,662,005 | 5/1987 | Grier-Idris | 2/9 |
| 4,672,968 | 6/1987 | Lenox et al. | 128/380 |
| 4,673,084 | 6/1987 | Hubbard et al. | 206/438 |
| 4,688,566 | 8/1987 | Boyce | 128/206.19 |
| 4,701,965 | 10/1987 | Landis | 2/428 |
| 4,702,240 | 10/1987 | Chaoui | 128/204.18 |
| 4,711,539 | 12/1987 | Krusas et al. | 351/63 |
| 4,802,473 | 2/1989 | Hubbard et al. | 128/206.19 |
| 4,848,330 | 7/1989 | Cowles | 128/200.24 |
| 4,848,334 | 7/1989 | Bellm | 128/207.11 |
| 4,848,366 | 7/1989 | Aita et al. | 128/863 |
| 4,920,960 | 5/1990 | Hubbard et al. | 128/206.12 |
| 4,941,470 | 7/1990 | Hubbard et al. | 128/206.13 |
| 4,944,310 | 7/1990 | Sullivan | 128/848 |
| 4,951,662 | 8/1990 | Townsend | 128/205.25 |
| 4,969,457 | 11/1990 | Hubbard et al. | 128/206.12 |
| 5,009,225 | 4/1991 | Vrabal | 128/201.23 |
| 5,020,533 | 6/1991 | Hubbard et al. | 128/206.23 |
| 5,054,480 | 10/1991 | Bare et al. | 128/201.25 |
| 5,054,481 | 10/1991 | Shin | 128/205.12 |
| 5,117,821 | 6/1992 | White | 128/206.15 |
| 5,150,703 | 9/1992 | Hubbard et al. | 128/206.12 |
| 5,165,395 | 11/1992 | Ricci | 128/202.22 |
| 5,322,061 | 6/1994 | Brunson | 128/206.13 |
| 5,383,450 | 1/1995 | Hubbard et al. | 128/206.23 |
| 5,433,192 | 7/1995 | Ebeling | 128/201.13 |
| 5,474,060 | 12/1995 | Evans | 128/204.22 |

(21)

5,694,927

DISPOSABLE MASK AND SUCTION CATHETER

BACKGROUND OF THE INVENTION

1. Field of the Invention

The present invention relates generally to surgical-type masks and, more particularly, to disposable surgical-type masks having a suction device associated therewith for removing exhaled air from behind the mask.

2. State of the Art

When operating with either surgical magnifying loupes or a microscope, most surgeons find it necessary to apply adhesive tape over the top edge of their surgical masks, across their cheeks and nose, in order to prevent fogging of the lenses from exhaled air. Removing this tape is very uncomfortable, particularly after doing it several times a day, and the surgeon is often left with a brilliant, annoying rash across his or her face. Moreover, the surgeon is often uncomfortable during surgery, and fatigue tends to occur more quickly.

Such problems with known surgical masks have, in the past, been addressed in several ways. One solution has been to reduce the temperature in the operating room so that the surgeons do not feel as hot. This solution, however, presents risk of complications for the patient from lowered body temperatures, particularly during long operations, and causes discomfort for others in the operating room, such as nurses and anesthesia crew members, who often must wrap themselves in blankets and extra gowns to avoid freezing.

Another solution has been to provide a reusable suction device that can be attached to the surgeon's mask to constantly evacuate exhaled air and draw fresh air into the mask. Such devices have, however, involved many parts and have been rather cumbersome.

Outside of the context of surgery, similar problems to those discussed above are experienced where, for whatever reason, one must wear corrective or protective eyewear and some manner of protective face mask at the same time, such as for work in dusty environments, where the phenomenon of fogging glasses due to exhaled air tends to occur. There is, accordingly, a need for some way of simply and inexpensively minimizing the effects of exhaled air behind masks, such as discomfort and fogged lenses, without the need for lowering room temperatures.

SUMMARY OF THE INVENTION

In accordance with one aspect of the present invention, a disposable mask and suction catheter is provided. The disposable mask and suction catheter includes a mask having a front side and a back side, the back side being disposed in contact with a user's face during use. The disposable mask and suction catheter also includes a catheter tube having a first and a second end, the first end being removably attachable to a suction source for removing exhaled air and the second end being attached to the back side of the mask.

BRIEF DESCRIPTION OF THE DRAWINGS

The features and advantages of the present invention are well understood by reading the following detailed description in conjunction with the drawing in which like numerals indicate similar elements and in which a disposable mask and catheter tube according to an embodiment of the present invention is shown schematically.

DETAILED DESCRIPTION OF THE PREFERRED EMBODIMENT

Figure 1:
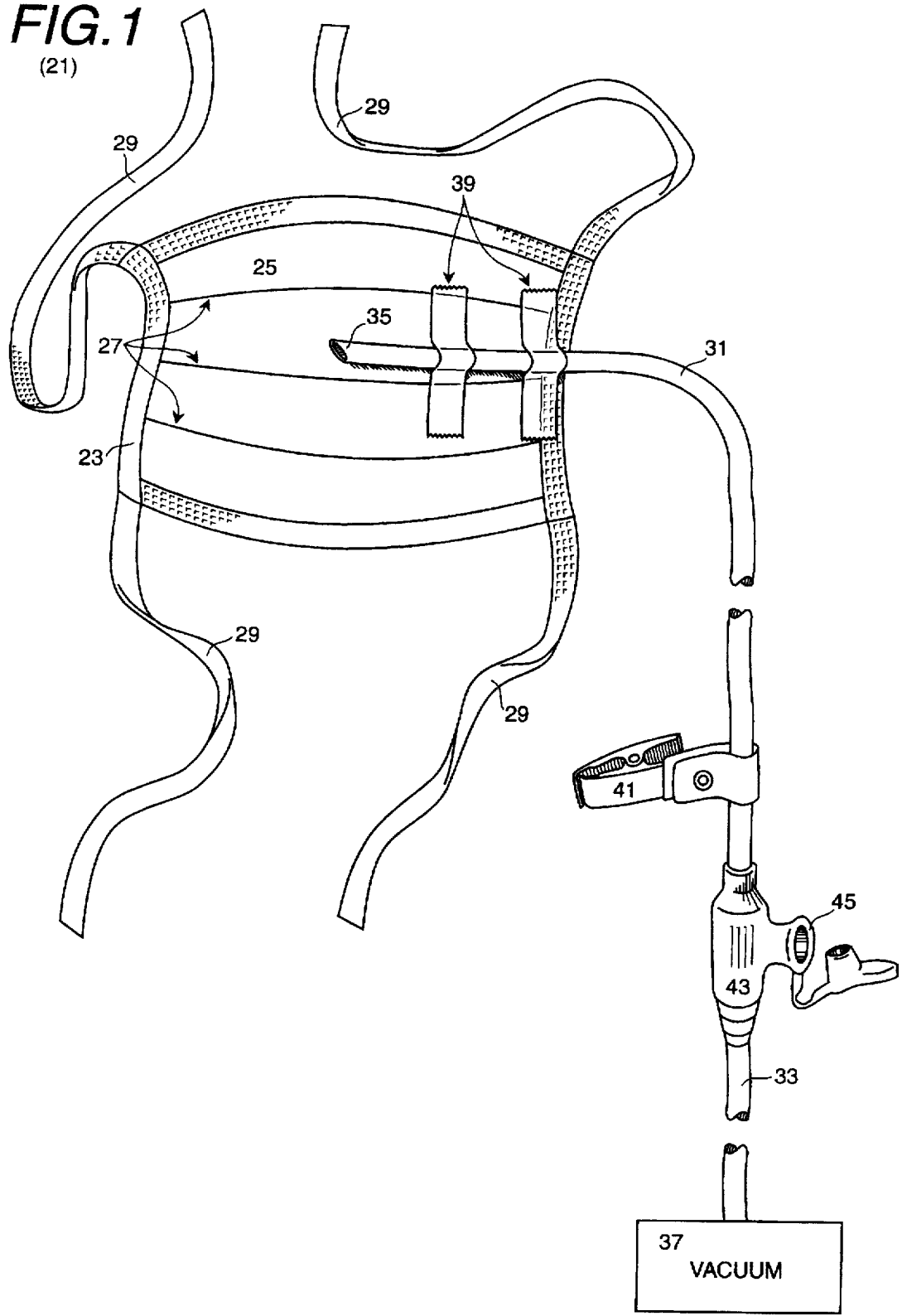

In FIG. 1, a disposable mask and suction catheter 21 according to a preferred embodiment includes a mask 23 having a front side (not shown) and a back side 25. As will be explained in more detail below, the back side 25 is to be disposed in contact with a user's face during use. The mask 23 is preferably of a generally conventional configuration, such as of the type used as a surgical mask or for protection in dusty or otherwise hazardous environments. As shown in the drawing, the mask 23 is formed from a sheet of material such as cotton having a plurality of pleats 27 to permit comfortable application of the mask over the face, and a number of tie cords 29 attached to the sheet.

The disposable mask and suction catheter also includes a catheter tube 31 having a first end 33 and a second end 35. The first end 33 is removably attachable to a suction source 37 for removing exhaled air. The second end 35 is attached, preferably permanently, to the back side 25 of the mask 23. The second end 35 of the catheter tube 31 is preferably attached to the back side 25 of the mask 23 by some simple, inexpensive means such as adhesive tape 39.

The catheter tube 31 is preferably a standard 14 French diameter suction catheter. Larger or smaller catheter tubes may be used, however, larger tubes provide undesired added weight and smaller tubes may not be of sufficient diameter to remove enough air from behind and around the mask to prevent fogging.

A device such as a clip 41 is preferably provided for removably attaching the catheter tube 31 to a user's clothing. The clip 41 is preferably mounted at some point along the length of the catheter tube 31 proximate the first end 33.

In the preferred embodiment, a device 43, such as a needle valve or other flow-varying means is adjacent to the first end 33 of the catheter tube 31 for adjusting a flow rate through the catheter tube 31 caused by the suction source 37. The flow-varying means 43 may be in the form of, for example, an openable and closable opening 45 in line with the catheter such that the suction source 37 tends to draw more air through the opening, when opened, than through the second end 35 of the catheter. If desired, multiple flow rate adjusting devices 43 may be provided in series with one another.

It will be appreciated that, because the above-described materials are relatively inexpensive and easily assembled, the disposable mask and catheter tube 21 according to the present invention can be constructed at minimal cost, yet provides greatly improved comfort for wearers of masks, particularly surgical-type masks. Also, the mask is readily removable without injury to the wearing face. Because of the ready availability of suction sources in operating-room environments, the disposable mask and catheter tube 21 has particular application in the context of surgical masks; however, the disposable mask and catheter tube can, of course, be used in any environment where wearing of a mask is necessary and a suction source is available.

It is, of course, possible to embody the invention in specific forms other than those described above without departing from the spirit of the present invention. The embodiments shown are merely illustrative and should not be considered restrictive in any way. The scope of the present invention is given in the appended claims, rather than the preceding description, and all variations and equivalents which fall within the ranger of the claims are intended to be embraced therein.

What is claimed is:

1. A disposable mask and suction catheter for preventing fogging of a user's glasses and providing desired cooling, comprising: a disposable pervious mask having a front side and a back side, the back side being disposed in contact with a user's face during use and allowing a user to breathe through the mask during an operation; and a length of relatively inexpensive lightweight suction catheter tubing having a first and a second end, the first end adapted to be connected to an available hospital operating room suction source for removing exhaled air, and the second end being in communication with the back side of the mask to receive exhaled air from a user, the catheter being of sufficient diameter to remove enough air to prevent fogging of a user's glasses and to provide increased comfort by drawing cool, dry air into the mask.

2. The disposable mask and suction catheter as set forth in claim 1, further comprising means for removably attaching the catheter tube to a user's clothing.

3. The disposable mask and suction catheter as set forth in claim 2, wherein the removable attaching means includes a clip.

4. The disposable mask and suction catheter as set forth in claim 1, wherein the second end of the catheter tubing is fixedly attached to the back side of the mask.

5. The disposable mask and suction catheter as set forth in claim 4, wherein the second end of the catheter tubing is fixedly attached to the back side of the mask by an adhesive tape.

6. The disposable mask and suction catheter as set forth in claim 1, further comprising flow rate adjusting means, attached to the catheter tubing, for adjusting a flow rate caused by the suction source.

7. The disposable mask and suction catheter as set forth in claim 6, wherein the flow rate adjusting means includes an openable and closable opening in line with the catheter tubing such that the suction source tends to draw more air through the opening, when opened, than through the second end of the catheter tubing.

8. The disposable mask and suction catheter as set forth in claim 6, wherein the flow rate adjusting means includes a valve.

9. The disposable mask and suction catheter as set forth in claim 7, wherein the flow rate adjusting means includes a needle valve.

10. The disposable mask and suction catheter of claim 1, wherein the catheter tube is a suction catheter of about 14 French diameter.

11. A method of removal of stale, humid air from a surgical mask in use as in claim 1, comprising the attachment of the first end of the suction catheter tubing to an available operating room suction source.

12. A method of removal of exhaled air from an area between a disposable mask and the face of the mask wearer, said mask having a suction catheter tube of about 14 French diameter attached at a second end to the mask, said second end of the catheter tube in communication with a backside of the mask for exhaust of said exhaled air, including attaching the first end of said catheter tube to an available, non-detachable suction source, exhausting the exhaled air from said area through the catheter tube and suction source and drawing fresh air into the area through the material of the mask.

13. A disposable mask and suction catheter, comprising: a disposable pervious mask having a front side and a back side, the back side being disposed in contact with a user's face during use and allowing the user to breath through the mask; and a length of relatively inexpensive lightweight suction catheter tubing having a first and a second end, the first end being removably attachable to a suction source for removing exhaled air and the second end being in communication with the back side of the mask to receive exhaled air from the user.

14. A disposable mask and suction catheter for preventing fogging of a user's glasses and providing desired cooling, comprising: a disposable pervious mask having a front side and a back side, the back side being disposed in contact with a user's face during use and allowing a user to breather through the mask during an operation; and a length of relatively inexpensive lightweight suction catheter tubing having a first and a second end, the first end adapted to be connected to an available hospital operating room wall suction source for removing exhaled air, and the second end being in communication with the back side of the mask to receive exhaled air from a user, the catheter being of sufficient diameter to remove enough air to prevent fogging of a user's glasses and to provide increased comfort by drawing cool, dry air into the mask.

15. The disposable mask and suction catheter as set forth in claim 14, further comprising means for removably attaching the catheter tube to a user's clothing.

16. The disposable mask and suction catheter as set forth in claim 15, wherein the removable attaching means includes a clip.

17. The disposable mask and suction catheter as set forth in claim 14, wherein the second end of the catheter tubing is fixedly attached to the back side of the mask.

18. The disposable mask and suction catheter as set forth in claim 17, wherein the second end of the catheter tubing is fixedly attached to the back side of the mask by an adhesive tape.

19. The disposable mask and suction catheter as set forth in claim 14, further comprising flow rate adjusting means, attached to the catheter tubing, for adjusting a flow rate caused by the available hospital operating room wall suction source.

20. The disposable mask and suction catheter as set forth in claim 19, wherein the flow rate adjusting means includes an openable and closable opening in line with the catheter tubing such that the available hospital operating room wall suction source tends to draw more air through the opening, when opened, than through the second end of the catheter tubing.

21. The disposable mask and suction catheter as set forth in claim 19, wherein the flow rate adjusting means includes a valve.

22. The disposable mask and suction catheter as set forth in claim 20, wherein the flow rate adjusting means includes a needle valve.

23. The disposable mask and suction catheter of claim 14, wherein the catheter tube is a suction catheter of about 14 French diameter.

24. A method of removal of stale, humid air from a surgical mask in use as in claim 14, comprising the attachment of the first end of the suction catheter tubing to an available hospital operating room wall suction source.

25. The available hospital operating room wall suction source as set forth in claim 14, wherein the suction source entails a vacuum force between 15–23" of mercury.

26. A method of removal of exhaled air from an area between a disposable mask and the face of the mask wearer, said mask having a suction catheter tube of about 14 French diameter attached at a second end to the mask, said second end of the catheter tube in communication with a backside of the mask for exhaust of said exhaled air, including attaching the first end of said catheter tube to an available, non-detachable, hospital operating room wall suction source, exhausting the exhaled air from said area through the catheter tube and available hospital operating room wall suction course and drawing fresh air into the area through the material of the mask.

27. A disposable mask and suction catheter, comprising:
a disposable pervious mask having a front side and a back side, the back side being disposed in contact with a user's face during use and allowing the user to breath through the mask; and a length of relatively inexpensive lightweight suction catheter tubing having a first and a second end, the first end being removably attachable to an available hospital operating room wall suction source for removing exhaled air and the second end being in communication with the back side of the mask to receive exhaled air from the user.

* * * * *